United States Patent [19]

Ishikawa et al.

[11] 4,057,061
[45] Nov. 8, 1977

[54] SANITARY NAPKIN

[75] Inventors: Shigemitsu Ishikawa, Kawanoe, Japan

[73] Assignee: Kabushiki Kaisha Angel, Iyomishima, Japan

[21] Appl. No.: 641,926

[22] Filed: Dec. 18, 1975

[30] Foreign Application Priority Data

Dec. 18, 1974 Japan .......................... 49-154054[U]
June 28, 1975 Japan ............................ 50-90876[U]

[51] Int. Cl.² .......................................... A61F 13/16
[52] U.S. Cl. ............................... 128/284; 128/290 R; 128/290 P; 128/296
[58] Field of Search .................. 128/284, 287, 290 P, 128/290 R, 296, 263, 290 B; 428/475, 510

[56] References Cited

U.S. PATENT DOCUMENTS

| | | | |
|---|---|---|---|
| 3,395,708 | 8/1968 | Hervey et al. | 128/284 |
| 3,461,871 | 8/1969 | Foote | 128/284 |
| 3,521,638 | 7/1970 | Parrish | 128/284 |
| 3,545,441 | 12/1970 | Gravdahl | 128/284 |
| 3,547,930 | 12/1970 | Blomquist et al. | 128/284 |
| 3,612,054 | 10/1971 | Matsuda | 128/287 |
| 3,666,611 | 5/1972 | Joa | 128/290 P |
| 3,765,417 | 1/1973 | Crockford | 128/263 |
| 3,768,480 | 10/1973 | Mesek | 128/287 |
| 3,779,246 | 12/1973 | Mesek | 128/287 |
| 3,911,921 | 10/1975 | Svensson | 128/290 R |

Primary Examiner—Aldrich F. Medbery
Attorney, Agent, or Firm—Armstrong, Nikaido & Marmelstein

[57] ABSTRACT

A thin sanitary napkin comprising an absorbent core, a fluid-barrier sheet covering at least the bottom surface of the absorbent core and a fluid-pervious wrapper enclosing the core and the sheet, the absorbent core being a compressed element which comprises cottony pulp compressed in a compression ratio of ½ to 1/10 to a thickness of about 1 to about 5 mm. The sanitary napkin not only is handy to carry about but also has a good fluid-absorbability, fluid-holding capacity and pleasant feeling in use, though it has about a half of one-third thickness of conventional sanitary napkins.

7 Claims, 9 Drawing Figures

SANITARY NAPKIN

BACKGROUND OF THE INVENTION

The present invention relates to a novel sanitary napkin, and more particularly to a thin sanitary napkin including, as an absorbent core, a compressed element which is made of cottony pulp and has a thickness of about 1 to about 5 mm.

Commercially available sanitary napkins generally comprise an absorbent core, the bottom of which is covered with a fluid-barrier sheet, and a fluid-pervious wrapper enclosing the absorbent core. In the above-mentioned sanitary napkins, soft cottony pulp having a good fluid-absorbability and fluid-holding capacity is usually employed as an absorbent core. Such a sanitary napkin, however, becomes relatively thick (normal thickness: about 10 to about 18 mm.) because it is necessary to employ cottony pulp having a thickness of about 8 to about 15 mm. in order to give thereto a good fluid-absorbability and fluid-holding capacity. Therefore, the thick sanitary napkin not only is bulky to carry about but also gives an unpleasant feeling to a user. Further, the thick sanitary napkin requires high cost for transporting or packing because of its large volume. However, hitherto there has never been obtained a satisfactory sanitary napkin which is able to eliminate the above-mentioned disadvantages.

OBJECTS OF THE INVENTION

It is an object of the present invention to provide a thin sanitary napkin which has a good fluid-absorbability and fluid-holding capacity, in spite of having about a half to one-third thickness of conventional sanitary napkins, and not only in handy to carry about but also gives a pleasant feeling to a user.

Further object of the invention is to provide a thin sanitary napkin which is so steady that the central part thereof does not deform due to wrinkles in use, whereby a leak of fluid therethrough does not occur.

Another object of the invention is to reduce expense such as cost for transporting or packing.

These and other objects of the present invention will be apparent from the following descriptions.

DETAILED DESCRIPTION

It has now been found that the above-mentioned objects are accomplished by employing, as an absorbent core, a novel compressed element prepared by compressing cottony pulp to the specified thickness in the specified compression ratio.

The sanitary napkin of the present invention is hereinafter explained by means of referring the drawings.

Figure 1A:
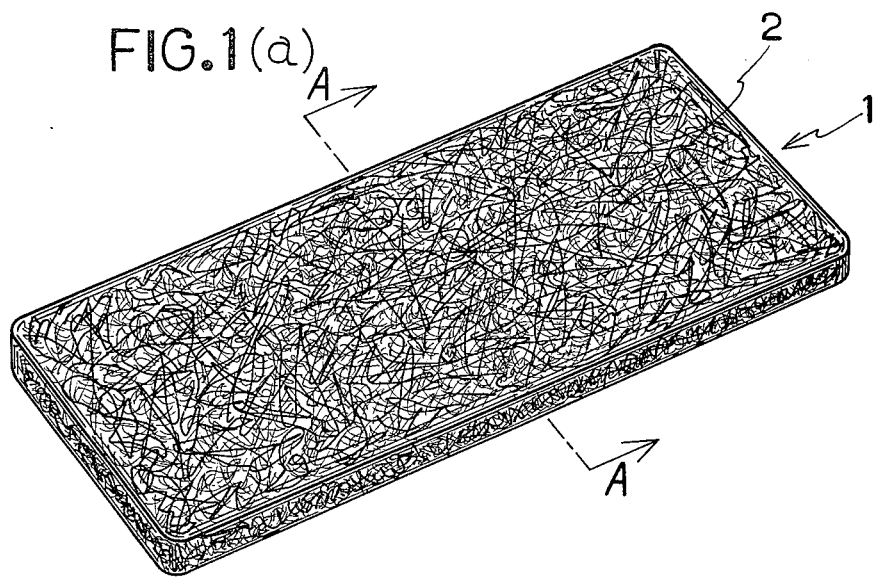
FIG. 1(a) is a perspective view showing an embodiment of the compressed element employed as an absorbent core in the present invention.
Figure 1B:
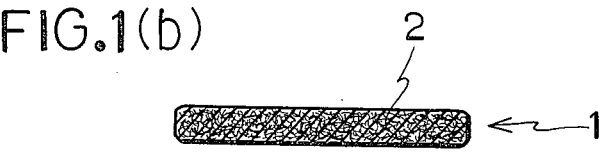
FIG. 1(b) is a cross-sectional view showing the compressed element of FIG. 1(a) taken along the line A—A of FIG. 1(a).

According to the embodiment of the compressed element shown in FIGS. 1(a) and 1(b), the compressed element employed as an absorbent core in the invention comprises cottony pulp 2 which is compressed to a thickness of about 1 to about 5 mm. in a compression ratio of ½ to 1/10. The term "a compression ratio of ½ to 1/10" in this specification means that a thickness of cottony pulp is compressed to about a half to one-tenth thickness.

The compressed element 1 is prepared by piling cottony pulp on a supporting web, if necessary, further piling thereon another supporting web, and then compressing thus obtained two- or three-layer structure by means of a compressing machine such as rolling mill. The supporting web is provided in order to make compression of cottony pulp easy, and is usually removed after compression. Therefore, the quality thereof is not limitative. Since it is a troublesome operation to remove the supporting web after compression, a fluid-pervious supporting web such as rayon paper is preferably employed as the supporting web provided on the upper surface (absorbent surface) of cottony pulp and either the above-mentioned fluid-pervious supporting web or a fluid-barrier supporting web such as waterproof paper which is able to prevent fluid from leaking in use is employed as the supporting web provided on the back surface of cottony pulp, so as to have no need of removing these supporting webs from cottony pulp after compression. These supporting webs are not shown in FIGS. 1(a), and 1(b).

When cottony pulp is compressed, it is essential that a compression pressure and an amount of cottony pulp piled on the supporting web are adjusted so as to give a compressed element which has a thickness of about 1 to about 5 mm. and a compression ratio of ½ to 1/10, preferably ⅓ to 1/10. The adjustment of the compression ratio of ½ to 1/10 is conducted by controlling the compression pressure within a range of 5 to 60 kg./cm². After the adjustment of the compression ratio, an amount of cottony pulp piled on the supporting web is determined by reverse calculation from the compression ratio so as to give a compressed element having a thickness of about 1 to about 5 mm.

It is understood that, when cottony pulp is compressed under the above-specified pressure, it should be piled in height of about 2 to about 50 mm. in order to give the compressed element having a thickness of about 1 to about 5 mm. It is particularly preferable that a cottony pulp is piled in weight of 2.5 to 7.5 g. per 100 cm². For instance, a compressed element having a thickness of about 3 mm. and a compression ratio of 1/5 is prepared by adjusting the pressure to 10 kg./cm². so as to give a compression ratio of 1/5 and then compressing the cottony pulp piled on the supporting web in height of about 15 mm. (in weight of about 3.5 g./100cm².) under the above-adjusted pressure.

The compressed element having a thickness of about 1 to about 5 mm. and a compression ratio of ½ to 1/10 is considerably thin in comparison with an absorbent core employed in conventional sanitary napkins, but the amount of cottony pulp piled on the supporting web is as much as or more than that of cottony pulp employed as an absorbent core of conventional sanitary napkins.

The compressed element also includes much space between pulp fibers, since the space is crushed in some degree in the direction of compression (thickness) but not in the direction of length and width at all. Besides, the compressed element is able to swell slowly in the direction of thickness when it receives fluid therein. The compressed element, therefore, can rapidly absorb fluid and can hold it therein. Further, the compressed element is soft to the touch and does not give an unpleasant feeling to a user.

The reason why the compressed element employed as an absorbent core in the present invention has the above-mentioned advantages is that the specified amount of cottony pulp on the supporting web is compressed under the specified pressure in order to give the compressed element having a thickness of about 1 to about 5 mm. and a compression ratio of ½ to 1/10.

If the compression ratio and/or the thickness of the compressed element are out of the above-specified range, there are occured some troubles mentioned hereinafter. That is to say, if the compression ratio and the thickness of the compressed element are more than 1/10 and 5 mm., respectively, the compressed element has a poor fluid-absorbability in the direction of compression and is hard to the touch, since the space between pulp fibers is substantially crushed in the direction of compression owing to excessive compression. Further, in order to give such element, cottony pulp must be piled on the supporting web in height of more than 50 mm. before compression so that an amount of cottony pulp employed relatively increases, which is an economical disadvantage. On the other hand, if the compression ratio and the thickness of the compressed element are less than ½ and 1 mm., respectively, the compressed element has a good fluid-absorbability and softness, but has such disadvantage that a fluid-holding capacity is insufficient due to a small amount of cottony pulp employed.

Figure 2A:
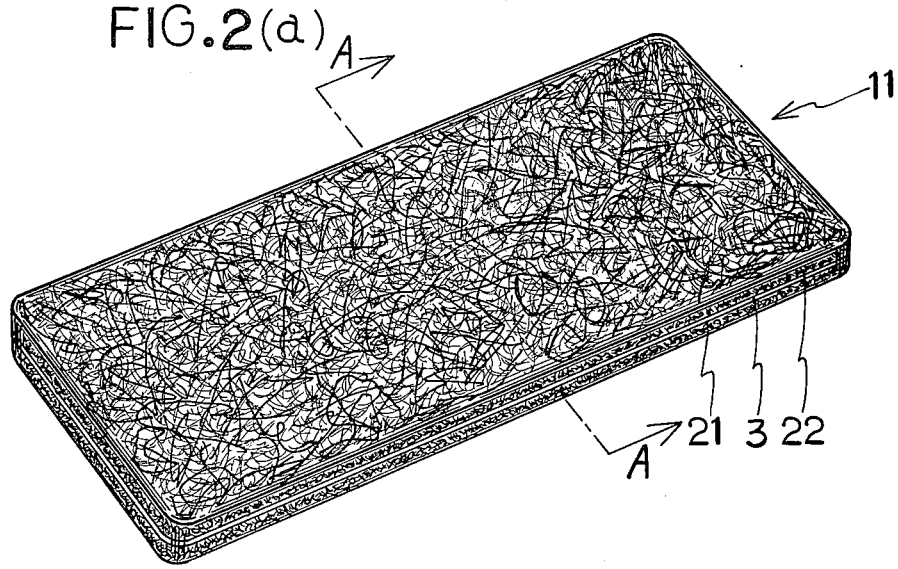
FIG. 2(a) is a perspective view showing another embodiment of the compressed element employed as an absorbent core in the present invention.
Figure 2B:
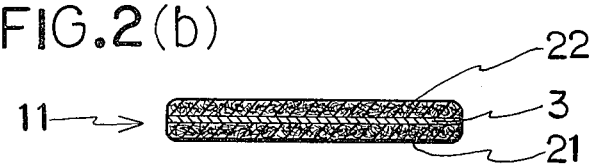
FIG. 2(b) is a cross-sectional view showing the compressed element of FIG. 2(a) taken along the line A—A of FIG. 2(a).

FIGS. 2(a) and 2(b) show another embodiment of the compressed element employed as an absorbent core in the present invention. The compressed element 11 shown in FIGS. 2(a) and 2(b) is a sandwich-structure comprising the fluid-absorbent paper 3 inserted between the under cottony pulp layer 21 and the upper cottony pulp layer 22. The absorbent paper 3 is similar in shape to cottony pulp layers 21 and 22, and an area thereof is equivalent to or smaller than cottony pulp layers 21 and 22. It is necessary to employ one to five sheet(s) of absorbent paper, preferably two to four sheets of absorbent paper, because the compressed element becomes hard to the touch when more than five sheets of absorbent paper are employed. The absorbent paper 3 inserted between cottony pulp layers 21 and 22 is not easily compressed and functions as a supporter for compression, so that less pressure can be employed in compression in comparison with that employed in compression of only cottony pulp. Further, the compressed element 11 is steady in the direction of width due to the function of the absorbent paper 3, so that the central paper thereof does not deform due to wrinkles in use, whereby a leak of fluid therethrough does not occur.

The compressed element 11 having the above-mentioned advantages is prepared by piling the absorbent paper 3 on the under cottony pulp layer 21, further piling the upper cottony pulp layer 22 thereon to give a sandwich-structure and then compressing the sandwich-structure to a thickness of about 1 to about 5 mm. in a compression ratio of ½ to 1/10 by the above-mentioned compression method. In that case, the above-mentioned supporting web may, of course, be provided on the upper surface of the cottony pulp layer 22 and the under surface of the cottony pulp layer 21. It is preferable that the quantitative ratio of cottony pulp of the under layer 21 and that of the upper layer 22 is within a range of 5 : 1 to 1 : 5 in order to prevent the absorbent paper 3 from getting near to either the under side or the upper side of the compressed element.

Figure 3:
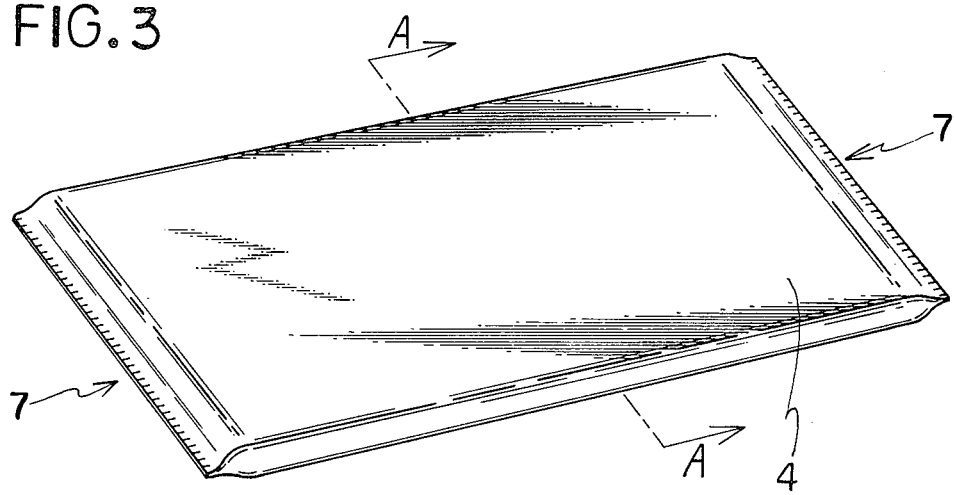
FIG. 3 is a perspective view showing an embodiment of the sanitary napkin of the present invention.
Figure 4A:
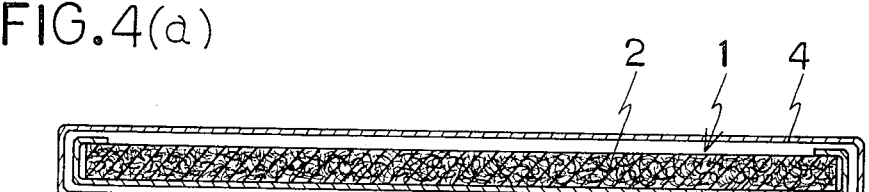
FIGS. 4(a), 4(b), 4(c) and 4(d) are cross-sectional views showing embodiments of the sanitary napkin as in FIG. 3 taken along the line A—A of FIG. 3, respectively.
Figure 4B:
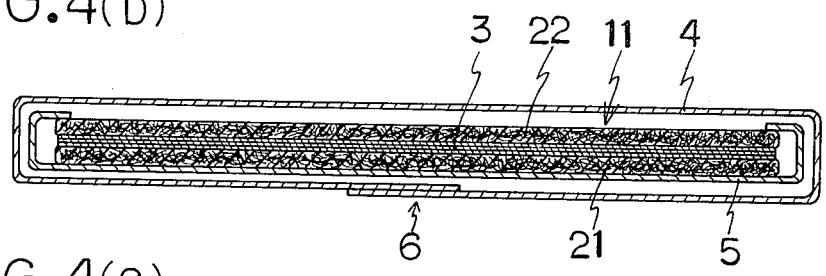

The sanitary napkin of the present invention has such an external appearance as shown in FIG. 3 and, as shown in FIG. 4(a) or 4(b), comprises the above-mentioned compressed element 1 or 11, the fluid-barrier sheet 5 covering at least the bottom of the element 1 or 11 and a fluid-pervious wrapper 4 enclosing the element and the sheet.

The preferable fluid-barrier sheet employed in the present invention includes waterproof paper, resinous film such as polyethylene film, polypropylene film, polyvinyl chloride film, nylon film or polyvinyl alcohol film and waterproof paper laminated with the above-mentioned resinous film. Though any fluid-pervious wrapper having a proper degree of strength in dry and in wet can be employed without any limitation, a wrapper such as commercially available nonwoven fabric, rayon paper, or the like is preferably employed.

The part 6 where the wrapper 4 overlaps at the bottom of the sanitary napkin and the both end parts 7 of the wrapper 4 in the direction of width are bonded with proper adhesives or with cotton thread or fabric impregnated with adhesives. In case the wrapper includes therein thermoplastic resin fiber or binder material, the both end parts 7 can be sealed by means of heat-pressure.

Figure 4C:
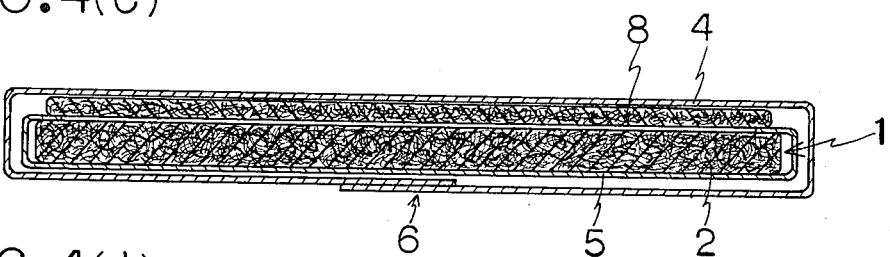
Figure 4D:
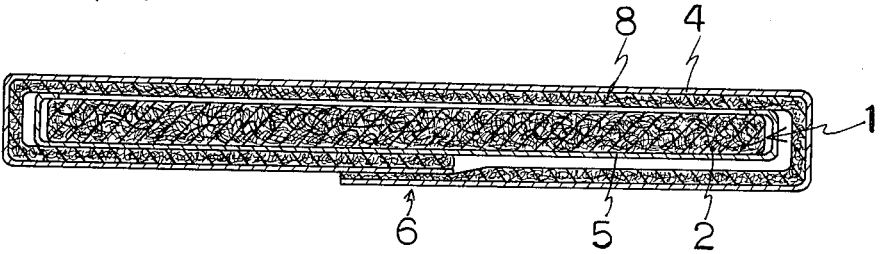

The sanitary napkin of the present invention includes not only the above-mentioned basic embodiment as shown in FIG. 4 (a) or 4(b) but also various modification of the embodiment as shown in FIG. 4(c) or 4(d). That is to say, FIG. 4(c) shows other modification of the sanitary napkin, wherein the cotton 8 is provided in a form of thin layer on the upper surface (absorbent surface) of the compressed element 1 and FIG. 4(d) shows another modification of the sanitary napkin, wherein a wrapper holding cotton 8 attached to the inner surface thereof is employed. These sanitary napkins become more soft to the touch due to the function of cotton 8 and give a more pleasant feeling to a user. Cotton which comprises natural fiber, regenerated fiber such as rayon staple or synthetic fiber such as polypropylene fiber and has a good fluid-pervious property, is preferably employed in the present invention. It is preferable that such cotton is provided in a form of thin layer having a thickness of not more than 1.5 mm. on the upper surface of the compressed element or the inner surface of the wrapper, since the sanitary napkin becomes too thick to accomplish the above-mentioned objects of the invention when cotton is provided in a form of layer having a thickness of more than 1.5 mm.

The sanitary napkin of the present invention has a thickness of about 3 to about 7 mm. (i.e., about a half to one-third thickness of conventional sanitary napkins) and is very handy to carry about. It also has a sufficient softness and gives a pleasant feeling in use to a user. Further, the sanitary napkin has such economical advantages that cost of packing material can be reduced due to small volume of a package in which several tens of the sanitary napkins are packed and that cost of transporting can be reduced since a great many sanitary napkins can be transported at once.

The sanitary napkin of the present invention is explained by means of the following illustrative Examples.

EXAMPLE 1

Cottony pulp was uniformly piled in height of about 5 mm. on a continuous rayon paper having a width of 7 cm., and a continuous rayon paper having a width of 7 cm. was further piled on cottony pulp. Thus piled was compressed under the pressure of 10 kg./cm$^2$. by means of a rolling mill to give a compressed continuous element having a compression ratio of 1/5 and a thickness of about 3 mm.

The side surface in the direction of width and the under surface of the compressed element are covered with a continuous waterproof paper having a width of 11 cm. and then thus covered was cut at intervals of 17 cm. by means of a cutting machine. Thus obtained was wrapped with a continuous rayon paper having a width of 18 cm. and was sealed at intervals of 20 cm. by means of heat-pressure, and then was cut at the sealed part thereof to give a sanitary napkin having a width of about 7 cm., a length of about 20 cm. and a thickness of about 5 mm.

Thus obtained sanitary napkin was soft to the touch.

EXAMPLE 2

Cottony pulp was uniformly piled in height of about 5 mm. on a continuous rayon paper having a width of 7 mm. and three sheets of absorbent paper were piled thereon, and further cottony pulp was piled on the absorbent paper in height of about 5 mm. and further rayon paper having a width of 7 cm. was piled thereon. Thus piled was compressed under a pressure of 40 kg./cm$^2$. by means of a rolling mill and was cut at intervals of 20 cm. by means of a cutting machine to give a compressed element having a compression ratio of $\frac{1}{8}$, a width of 7 cm. a length of 20 cm. and a thickness of about 1.5 mm.

The side surface in the direction of width and the under surface of the obtained compressed element were covered with a rectangular polyethylene film having a width of 10 cm. and a length of 20 cm. and then thus covered was wrapped with a rectangular nonwoven fabric having a width of 18 cm. and a length of 22 cm. Thus obtained was sealed at the both end parts in the direction of length by means of heat-pressure to give a sanitary napkin having a thickness of about 3.5 mm. The sanitary napkin is soft to the touch.

EXAMPLE 3

The same manner as in Example 1 was repeated except that cotton was piled in height of about 1mm. on the upper surface of the compressed element prior to be wrapped to give a sanitary napkin having a thickness of about 6 mm. Thus obtained sanitary napkin is soft to the touch.

EXAMPLE 4

The side surface and under surface of the compressed element obtained in Example 2 were covered with a polypropylene film, and then thus covered was wrapped with a nonwoven fabric which holds cotton provided in a form of layer having a thickness of about 1.5 mm. on the inner surface. Thus obtained was sealed at the end parts in the direction of length by means of heat-pressure to give a sanitary napkin having a thickness of about 4 mm. The obtained sanitary napkin is soft to the touch.

EXAMPLE 5

The water-holding capacity of each compressed element obtained in Examples 1 and 2 was determined by the following method.

[Method]

Water is sprinkled onto the upper surface (absorbent surface) of the compressed element set on a wire net so as to be absorbed by the compressed element as much as possible. The compressed element absorbing water is left as it is for a minute, and then the weight thereof is measured. The difference in weight between the compressed element absorbing water and the compressed element not absorbing water is calculated to determine the water-holding capacity.

The results are shown in the following Table.

| Example | Thickness of Compressed Element (mm.) | Water-holding Capacity (g.) |
| --- | --- | --- |
| 1 | 3.0 | 80 |
| 2 | 1.5 | 72 |
| Comparative Example | 10.0 | 78 |

COMPARATIVE EXAMPLE

A water-holding capacity of conventional absorbent core (thickness: about 10 mm., width: 70 mm., length: 170 mm.) which consists of non-compressed cottony pulp was determined in the same manner as in Example 5. The result is shown in the above Table.

As is clear from the above Table, though the compressed element employed as an absorbent core in the present invention is very thin, the water-holding capacity thereof is equivalent to or is greater than that of a conventional absorbent core.

What we claim is:

1. A sanitary napkin comprising an absorbent core, a fluid-barrier sheet covering at least the bottom surface of said core and a fluid-pervious wrapper enclosing said core and said sheet, said absorbent core being a compressed element which comprises cottony pulp compressed in a compression ratio of $\frac{1}{2}$ to 1/10 to a uniform thickness of about 1 to about 5 mm.

2. The sanitary napkin as defined in claim 1, wherein said compressed element has a weight of 2.5 to 7.5 g. per 100 cm$^2$.

3. The sanitary napkin is defined in claim 1, wherein said compressed element is a sandwich-structure comprising a fluid-absorbent paper inserted between an upper cottony pulp layer and an under cottony pulp layer.

4. The sanitary napkin as defined in claim 1, wherein said wrapper comprises a rayon paper.

5. The sanitary napkin as defined in claim 3, wherein a quantitative ratio of cottony pulp of said under layer and that of said upper layer is within a range of 5 : 1 to 1 : 5.

6. The sanitary napkin as defined in claim 3, wherein the number of said fluid-absorbent paper is 1 to 5.

7. The sanitary napkin as defined in claim 1, wherein said wrapper comprises a nonwoven fabric having cotton attached to the inner surface thereof.

* * * * *